United States Patent
Springhorn et al.

(10) Patent No.: US 6,551,499 B1
(45) Date of Patent: Apr. 22, 2003

(54) METHOD FOR MONITORING THE FUNCTION OF A GAS SENSOR AND/OR FOR REGENERATING THE SAME

(75) Inventors: Carsten Springhorn, Stuttgart (DE); Bernd Schumann, Rutesheim (DE); Sabine Thiemann-Handler, Stuttgart (DE)

(73) Assignee: Robert Bosch GmbH, Gerlingen-Schillerhoehe (DE)

( * ) Notice: Subject to any disclaimer, the term of this patent is extended or adjusted under 35 U.S.C. 154(b) by 0 days.

(21) Appl. No.: 09/856,911

(22) PCT Filed: Sep. 28, 2000

(86) PCT No.: PCT/DE00/03383

§ 371 (c)(1),
(2), (4) Date: Jun. 20, 2001

(87) PCT Pub. No.: WO01/23729

PCT Pub. Date: Apr. 5, 2001

(30) Foreign Application Priority Data

Sep. 30, 1999 (DE) .......................... 199 47 239

(51) Int. Cl.$^7$ ...................... G01N 27/41; G01N 27/407

(52) U.S. Cl. .................. 205/784.5; 204/401; 204/402; 73/1.06

(58) Field of Search ................ 204/401, 402, 204/425; 73/23.31, 23.32, 1.06, 1.07; 205/784.5

(56) References Cited

U.S. PATENT DOCUMENTS

| | | | |
|---|---|---|---|
| 4,532,013 A | | 7/1985 | Dietz et al. |
| 4,814,045 A | * | 3/1989 | Ohsuga et al. ........... 205/784.5 |
| 4,819,602 A | * | 4/1989 | Mieno et al. ............... 123/688 |
| 4,938,194 A | | 7/1990 | Kato et al. |
| 5,558,752 A | * | 9/1996 | Wang et al. ................ 204/401 |
| 5,769,063 A | * | 6/1998 | Mizusawa ................... 123/688 |
| 5,804,700 A | * | 9/1998 | Kwon et al. .............. 73/23.32 |
| 6,007,697 A | * | 12/1999 | Yagi et al. .................. 205/788 |

FOREIGN PATENT DOCUMENTS

| | | | | |
|---|---|---|---|---|
| EP | 0892265 | | 1/1999 | |
| GB | 2194056 A | * | 2/1988 | .......... G01N/27/28 |

OTHER PUBLICATIONS

"Thick Film ZrO2 NOx Sensor" by N. Kato et al, SAE Technical Paper Series, 960334, Feb. 26–29, 1996.

* cited by examiner

Primary Examiner—Robert J. Warden, Sr.
Assistant Examiner—Kaj K. Olsen

(57) ABSTRACT

This invention provides a method for monitoring the function and/or regeneration of a gas probe. The invention includes a measurement of first and second pump currents of the gas probe and a determination of a difference between the first and second pump currents (ΔI). If ΔI exceeds a pregiven value, then a saturation pump voltage is applied and the difference between a resulting pump current and a previously stored minimum pump current (ΔI plus) is determined. If ΔI plus exceeds a pregiven value, then a regeneration voltage is applied.

9 Claims, 3 Drawing Sheets (State of the Art)

METHOD FOR MONITORING THE FUNCTION OF A GAS SENSOR AND/OR FOR REGENERATING THE SAME

FIELD OF THE INVENTION

The invention relates to a method for monitoring the function and/or regeneration of a gas probe.

BACKGROUND OF THE INVENTION

Double chamber $NO_x$ limit current sensors for measuring the oxygen or nitrogen oxide concentration in the exhaust gas of motor vehicles have been known for some time and are described, for example, in the publication "SAE Technical Paper Series No. 960334" entitled "Thick Film $ZrO_2$ $NO_x$ Sensor". These sensors have an oxygen ion conducting ceramic, preferably zirconium oxide, which ceramic includes two compartments connected to the exhaust gas of the engine. Several electrodes are mounted in the exhaust gas as well as in the chambers. In a first chamber, the oxygen is electrochemically pumped away by means of two electrodes. This first chamber communicates directly with the exhaust gas of the engine via a porous region of the ceramic. A reduction of the oxygen molecules takes place on the cathode mounted in one chamber. In the oxygen-ion conducting ceramic, the oxygen ions, which arise in this manner, are transported because of the applied voltage to the anode which is mounted in the exhaust-gas flow and where a reversal of the reduction takes place, that is, oxygen molecules are formed from the oxygen ions by adding electrons. The consumed or regenerated electrons can then be measured as an electrical current.

A reduction of the flow density takes place because of deterioration after a longer duration of operation.

SUMMARY OF THE INVENTION

It is the task of the invention to provide a method for monitoring the function and/or regeneration of a gas probe of the kind described initially herein which makes possible a regeneration of the gas probe in dependence upon the detected operability.

The task is solved with the features of claim 1. The method of the invention affords the advantage that not only the function capability of the exhaust-gas probe is monitored but that a regeneration of the probe takes place when a deterioration of the exhaust-gas probe is determined. This regeneration is undertaken by applying a regeneration voltage which is greater than the saturation voltage.

The steps for checking the functioning capability of the probe and the application of the regeneration voltage is repeated several times, preferably five times, until there is a drop below a pregiven threshold value. A disturbance announcement is outputted when there is no drop below this threshold value.

As to the regeneration voltage, it can be of the same polarity as the pump voltage but it is also possible that it has a polarity opposite to the pump voltage. The regeneration voltage can be applied in the lean phase, in the rich phase, or even for an air number $\lambda=1$ of the engine.

Advantageously, the flow, which adjusts because of the application of the regeneration voltage, or another index for this current is measured, such as the time during which the regenerating voltage was applied, in order to set a diagnostic signal or to input a value into a fault memory of the sensor part.

DESCRIPTION OF THE PREFERRED EMBODIMENT OF THE INVENTION

Figure 1:
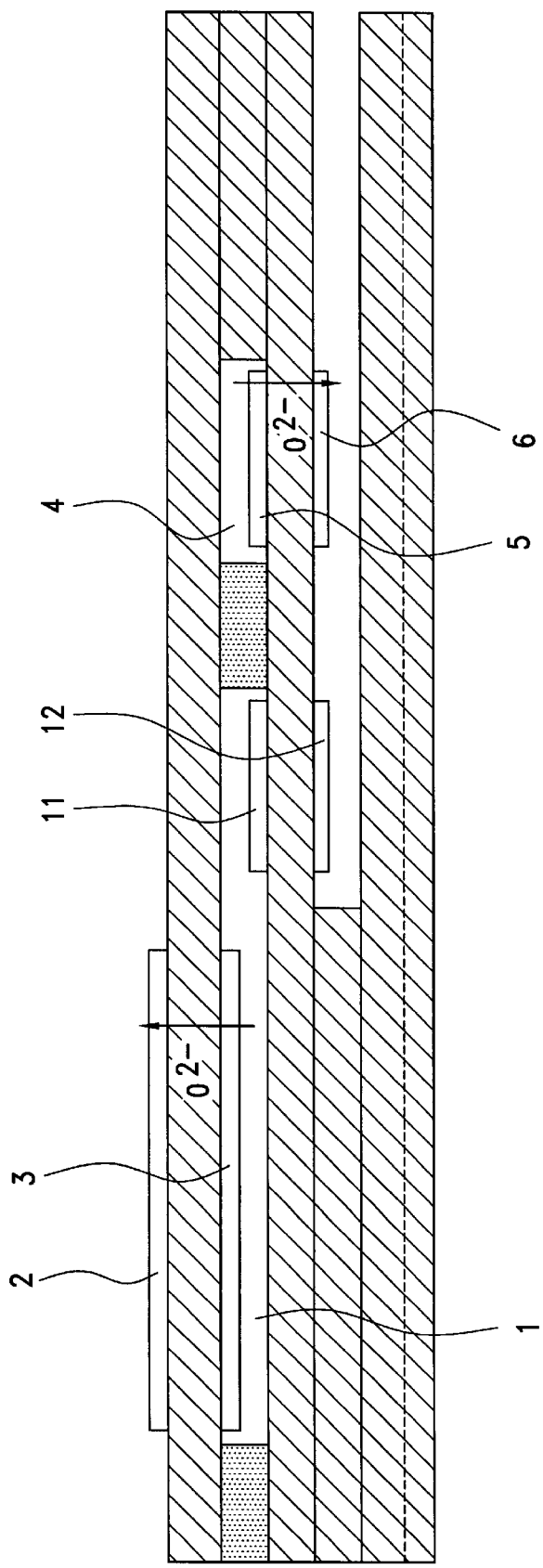
FIG. 1 is an $NO_x$ double chamber sensor known from the state of the art.

In FIG. 1, an $NO_x$ double chamber sensor is shown which is known per se. This sensor is presented, for example, in the publication "SAE Technical Paper Series No. 9603341", Nobuhido Kato, Kunihiko Nakagaki and Noriyuki Ina: "Thick Film $ZrO_2$ $NO_x$ sensor", starting at page 136, to which reference is made herein.

The sensor shown in FIG. 1 for automobile exhaust gases includes several layers of an oxygen-conducting ceramic, for example, $ZrO_2$. The sensor includes two chambers 1 and 4 which communicate with the exhaust gas via a layer of the oxygen ion conducting ceramic. A first electrode 2 is mounted in the exhaust gas of the engine and a second electrode 3 lies in the chamber 1 opposite the first electrode.

The first chamber communicates via a porous region of the oxygen ion conducting ceramic directly with the exhaust gas. In this first chamber 1, oxygen is electrochemically pumped away by means of electrodes (2, 3). The electrode 3 functions as a cathode and the following reaction (reduction) takes place there: $O_2$(gas phase)+4 $e^-$ (cathode)→2 $O^{2-}$ (oxygen ion conductor). In the oxygen ion conducting ceramic, $O^{2-}$ ions are transported to the electrode 2, which operates as an anode, because of the voltage applied to the electrodes (2, 3). At the electrode 2, the following reactions take place (reversal of the above reaction): 2 $O^{2-}$ (oxygen ion conductor)→$O_2$ (gas phase)+4 $e^-$ (anode). The consumed or regenerated electrons can be measured as an electrical current. The low oxygen concentration, which is adjusted by the outpumping in the first chamber 1, leads to a measurable voltage between two additional electrodes identified with reference numerals 11, 12. This voltage can serve to control the voltage applied between the electrodes 2, 3.

A second chamber 4 is connected to the first chamber via a porous portion of the ceramic. In the second chamber 4, $NO_x$ is removed with the aid of two additional electrodes 5, 6 of which one electrode 5 operates as a cathode and the other electrode 6 as an anode. $NO_x$ breaks down at the electrode 5 to $N_2$ and $O_2$. The oxygen is pumped off (reduction) as explained above. The electrodes 3 and 5 are produced from such a material that the $NO_x$, which is to be measured, is only reduced in the second chamber 4. The electrodes consist, for example, of platinum alloys or of platinum rhodium alloys.

At sufficiently high pump voltages, the electrical currents, which are to be measured, are limited (limit currents) by the porous portion operating as a diffusion barrier. This means that these currents do not increase further beyond a specific applied voltage (limit voltage). The electrical currents, which are to be measured above this limit voltage (less an offset current occurring in most cases), are then proportional to the concentrations of oxygen or nitrogen oxide existing in front of the particular chamber. The sensor is so operated that a voltage as small as possible is to be applied for the two chambers 1, 4. This voltage lies slightly higher than the limit voltage and is applied, for example, during continuous operation. A limit voltage as small as possible can be obtained with electrodes which are operated at a specific applied voltage which is less than the limit voltage and supplies electric currents as large as possible under defined external conditions.

Figure 2:
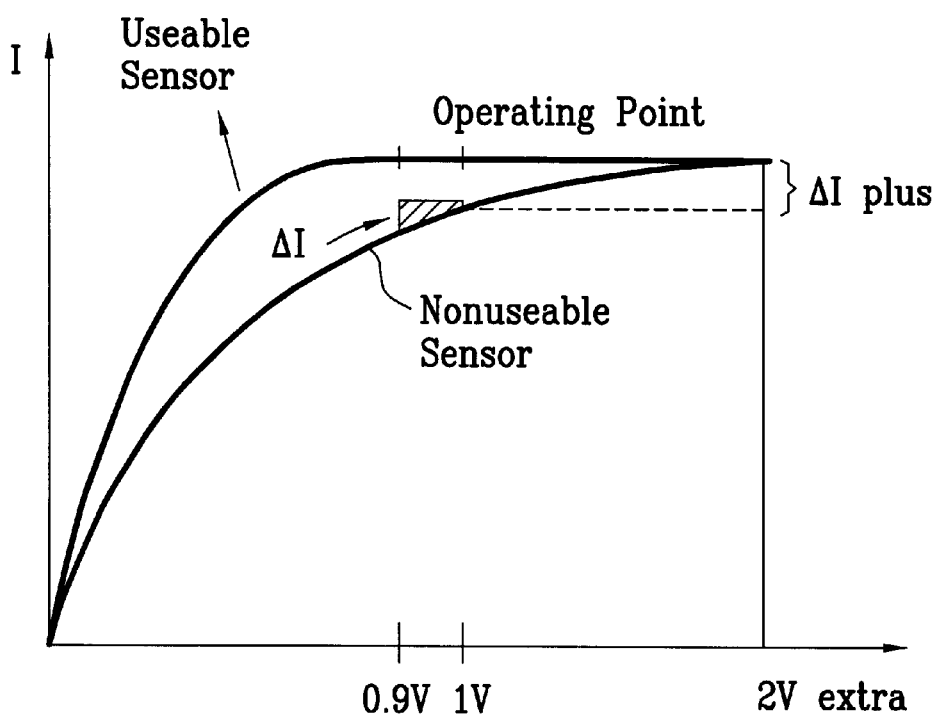
FIG. 2 schematically explains the method of the invention for checking the operability and/or regeneration of a gas probe with the flow taken off at the sensor plotted against the pump voltage; and, FIG. 3 is a circuit arrangement for carrying out the method of the invention.

In the following, a method for checking the functioning capability and/or regeneration of such an $NO_x$ double chamber sensor is explained in connection with FIGS. 1, 2 and 3.

A switch 9, for example, is used between the electrodes 2, 3 or 5, 6 and a current measuring device 7 provided therefore, on the one hand, and a pump source 8, on the other hand. With the switch 9, the electrodes 2, 3 or 5, 6 can be separated from the voltage source 8. The switch 9 is opened when, for a defined operating condition of the vehicle, a specific pump voltage is exceeded in the first/second chamber 1 or 4 by pumping off oxygen/nitrogen oxide or when the application of a lower voltage from the pump source yields a lower current than the current having the voltage used previously during continuous operation. The method includes the following steps:

a) First, a first pump voltage is applied, for example, 1 V (see FIG. 2) and the first pump current which adjusts is measured.

b) Then, a second pump voltage is applied which is higher or lower compared to the first pump voltage and the second pump current which adjusts is measured. For example, 0.9 V can be applied as a second pump voltage as shown schematically in FIG. 2.

c) Thereafter, the difference $\Delta I$ of the first and second pump currents is formed.

d) If this difference $\Delta I$ exceeds a pregiven value, which is stored, for example, in the current measuring device 7, a saturation pump voltage, which was determined previously experimentally, is applied and the pump current which then adjusts, is compared to a previously stored minimum pump current.

e) The difference ($\Delta I$ plus) of the minimum pump current and the pump current, which adjusts for the saturation pump voltage, is formed.

f) If this difference ($\Delta I$ plus) exceeds a pregiven amount, a regeneration voltage from a further external voltage source 10 is applied for a pregiven time, for example, 5 seconds. The regeneration voltage is greater than the saturation voltage.

The method steps (a) to (f) are repeated several times, for example, the steps are repeated five times until the amount of the difference of the first and second pump currents drops below a further pregiven threshold value, that is, until a previously fixed current density value or a fraction of this current density value is reached or, if this is not the case, a disturbance announcement is outputted.

In the last case, the sensor can no longer be regenerated and is unuseable.

With the method steps (a) to (d), a check is made as to whether a sensor has deteriorated. In this case, the difference $\Delta I$ of the first and second pump currents deviates from the pregiven and stored value. With the steps (d) to (f), it is first checked as to whether the sensor can at all be regenerated. This is the case, when the difference of the minimum pump current and of the pump current, which is adjusted at the saturation pump voltage, exceeds a pregiven amount. If this is the case, the regeneration is performed for a certain time (for example, 5 seconds) by applying the regeneration voltage which is significantly higher than the saturation voltage and is, for example, as shown above, 7 V compared to 2 V saturation voltage. It is understood that the regeneration voltage can be determined in dependence upon the difference ($\Delta I$ plus) as well as in dependence upon the difference ($\Delta I$). The regeneration voltage can be of the same or changing polarity as the pump voltage and can be applied in lean or in rich operating states or even for an air number $\lambda=1$.

Furthermore, the time in which the regeneration voltage is applied to the electrodes can be extended and measured. This time or even the obtained current value can be announced to a control apparatus in order to set a diagnostic signal or to input a value (not shown) into a fault memory of the sensor part.

Figure 3:
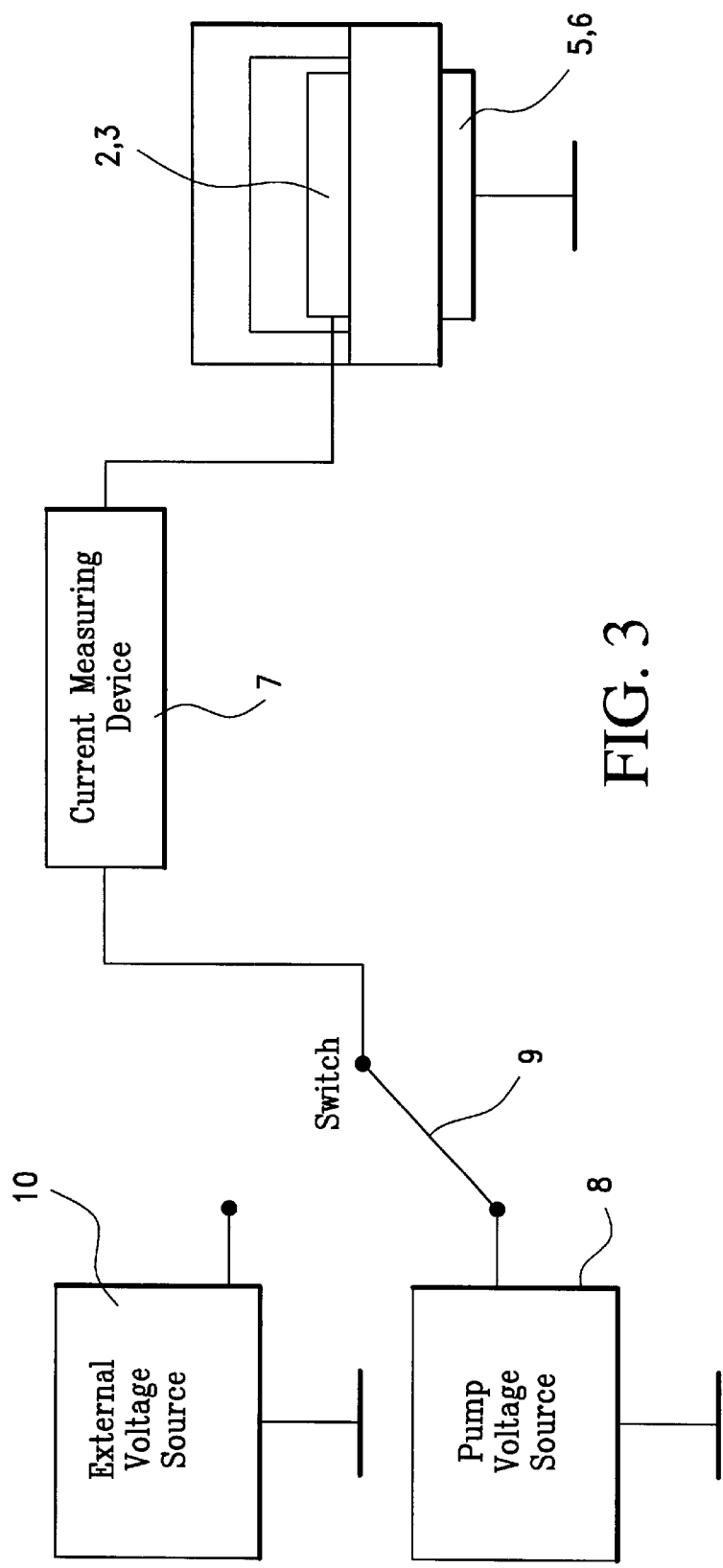

As shown in FIG. 3, the external voltage source 10 can be connected to the electrodes 2, 3 or 5, 6 of the $NO_x$ sensor by reversing the switch 9. In this case, the pump voltage source 8 is decoupled. It is understood, however, that the external voltage source 10 can also be provided as part of the pump voltage source 8. The pump voltage source 8 must then be correspondingly designed to a higher power in order to make possible the above-described regeneration of the sensor.

What is claimed is:

1. A method for monitoring the function and/or regeneration of a gas probe, the gas probe including: a heatable probe ceramic which detects gas molecules, a first pump electrode arranged in a chamber, and a second pump electrode arranged in the exhaust gas of the engine, the method comprising the steps of:

a) providing a pump voltage source and applying a pump voltage across the first and second pump electrodes so that an oxygen partial pressure is adjusted in the interior of said chamber by electrochemically pumping away the oxygen molecules;

b) applying a first pump voltage and measuring a first pump current;

c) applying a second pump voltage, which is higher or lower compared to the first pump voltage, and measuring a second pump current;

d) forming the difference ($\Delta I$) of the first and second pump currents;

e) if the difference ($\Delta I$) exceeds a pregiven value, applying a previously determined saturation pump voltage and comparing a resulting pump current to a previously stored minimum pump current;

f) forming the difference of the minimum pump current and of the resulting pump current ($\Delta I$ plus); and g) if the difference ($\Delta I$ plus) of the minimum pump current and of the resulting pump current exceeds a pregiven amount, applying a regeneration voltage, wherein the is generated by a further pump source, which regeneration voltage is greater than the saturation voltage.

2. The method of claim 1, repeating steps (b) to (g) until the amount of the difference of the first and the second pump currents ($\Delta I$) drops below a further pregiven threshold value or, if this is not the case after repeating several times, outputting a disturbance announcement.

3. The method of claim 2, wherein said steps (b) to (g) are repeated five times.

4. The method of claim 2, wherein the regeneration voltage is of the same polarity as the pump voltage.

5. The method of claim 1, wherein the regenerative voltage is of an opposite polarity than the pump voltage.

6. The method of claim 1, wherein the regeneration voltage is applied in the lean operating phase of the engine.

7. The method of claim 1, wherein the regeneration voltage is applied in the rich operating phase of the engine.

8. The method of claim 1, wherein the regeneration voltage is applied for an air number $\lambda=1$ of the engine.

9. The method of claim 1, wherein an index of the current, which adjusts with the application of the regeneration voltage, is measured and is stored in a memory.

\* \* \* \* \*